United States Patent [19]

Cheetham

[11] 4,426,726

[45] Jan. 17, 1984

[54] APPARATUS AND METHOD FOR X-RAY BEAM ALIGNMENT

[76] Inventor: Eric C. Cheetham, 565 4th Ave., Elizabeth, N.J. 07202

[21] Appl. No.: 351,417

[22] Filed: Feb. 23, 1982

[51] Int. Cl.³ .................. G01N 21/00; G03B 41/16
[52] U.S. Cl. .................................. 378/206; 378/207
[58] Field of Search ...................... 378/205, 206, 207

[56] References Cited

U.S. PATENT DOCUMENTS

| | | | |
|---|---|---|---|
| 3,909,616 | 9/1975 | Redfield et al. | 378/205 |
| 4,242,587 | 12/1980 | Lescrenier | 378/206 |
| 4,356,400 | 10/1982 | Polizzi et al. | 378/205 |

FOREIGN PATENT DOCUMENTS 1021814  12/1952  France ............................... 378/206

OTHER PUBLICATIONS

Gaskill, J. D., *Linear Systems, Fourier Transforms, and Optics*, Wiley, 1978, pp. 479-484.

*Primary Examiner*—Alfred E. Smith
*Assistant Examiner*—T. N. Grigsby

[57] ABSTRACT

An apparatus and method are disclosed for aligning the center of an X-ray beam with both a reference point on a patient and the center of the X-ray film holder. An X-ray collimator is provided with a visible light source and two fan beam assemblies which provide two fan beam planes. The fan beam planes perpendicularly bisect the X-ray beam and each other to form a line of intersection corresponding to the center of the X-ray beam. The intersecting fan beam planes form a cross-hair reticle whose origin point of intersection lies on the center of the X-ray beam. The cross-hair reticle is directed toward a patient for positioning the patient with respect to the X-ray beam. For purposes of aligning the X-ray beam, the cross-hair reticle may be aimed at an opaque object located at the center of the X-ray film holder. In this way, both the center of the X-ray film holder and the point of intersection of the cross-hair reticle are in alignment with the center of the X-ray beam. The preferred light source is a laser beam forming a laser reticle. A single source may be used to provide two fan beam planes; or two separate laser sources may be used. The width of the fan beams emerging from the apparatus of the invention is controlled by beam diaphragms in order to confine the cross-hair reticle to the surface of the patient.

5 Claims, 3 Drawing Figures

APPARATUS AND METHOD FOR X-RAY BEAM ALIGNMENT

BACKGROUND OF THE INVENTION

The present invention relates to the field of medical X-ray technology, and more particularly to an apparatus and a method for aligning the center of an X-ray beam with both a reference point on a patient and with the center of the X-ray film holder.

Obtaining accurate X-rays at reasonable cost with minimum inconvenience to the patient and the X-ray technologist is a constantly sought after goal. An important factor in obtaining a suitable X-ray is good positioning of the X-ray apparatus with respect to both the patient and the X-ray film holder or bucky. Effective positioning avoids the inconvenience and expense of sending a patient back for an additional X-ray because the initial X-ray was unsuitable as a result of poor machine alignment.

Devices in the prior art have been described with the object of obtaining good positioning of the patient with respect to the X-ray beam. In U.S. Pat. No. 3,629,594, a device is disclosed for monitoring the position of a patient during exposure to a high energy diagnostic or therapeutic beam. A piece of retroreflective tape is placed on or near the patient, and reflected energy is monitored by a sensor-controlled monitoring device. If the patient moves, reflection ceases and the sensor detects this condition. The monitoring device then turns off the high energy beam. The monitoring device can be mounted on the carriage of the high energy source. The monitoring device, however, does not aid in aiming the X-ray beam to the center of the X-ray film holder. Furthermore, the apparatus requires complex electronic circuitry for monitoring the patient and controlling the X-ray beam.

In U.S. Pat. No. 3,861,807, a device is disclosed for monitoring the position of a patient during exposure to a high energy X-ray beam. The center axis of the X-ray beam coincides with the center of a family of visible marker light concentric circles. A two way mirror is interposed between the X-ray source and the patient and is employed to add the marker circles to the path of the X-ray beam.

Other patents which use a two way mirror to add a visible marker beam to the path of an X-ray beam are U.S. Pat. Nos. 2,955,205 and 4,167,675. An undesirable feature of apparatus employing two way mirrors in the path of an X-ray beam is that a higher level of X-radiation is required to be transmitted through the mirror on its way to the patient.

In U.S. Pat. No. 3,708,663, a device is disclosed in which a cross-beam visible light projector is attached to an X-ray machine in such a manner that the axes of the light beam projector and the X-ray machine are disposed in the same horizontal plane. The X-ray beam and the visible light beam from the projector are always synchronized so that the horizontal light beam and the central X-ray beam are in the same horizontal plane. The beam marker does not coincide with the center of the X-ray beam but is calibrated with an auxiliary target to cause the axis of the X-ray beam to intersect the patient at a selected reference point.

U.S. Pat. No. 4,132,900 discloses an optical pointer for a radiographic apparatus in which two laser beams are projected through cylindrical lenses to provide planar divergent or fan-shaped beams of light which intersect to form a line substantially coincident the central axis of the X-radiation beam. The laser beams originate from laser sources outside and below the housing for the X-ray beam and below the table the patient lies upon. Because the fan-shaped beams originate below the level of the patient, they do not fall upon the upper surface of a patient lying on the table. Thus, the fan-shaped beams cannot be readily used to position the patient as he is lying in the table. Each of the fan-shaped beams intersects the center axis of the X-ray beam and also intersects the other fan-shaped beam. The plane of intersection of the two fan-shaped beams coincides with the axis of the X-ray beam. However, the fan-shaped beams are generated essentially perpendicular to the center axis of the X-ray beam and propagate in large measure into the room and are not confined to the patient only. Having stray laser radiation traversing the entire room is potentially hazardous to both the patient and the X-ray machine operator.

The problem of not having the central X-ray beam in alignment with the center of the X-ray film holder is a serious one and often prevents obtaining adequate X-rays.

SUMMARY OF THE INVENTION

Accordingly, it is a primary object of the present invention to provide an apparatus and a method of aligning the center of an X-ray beam with both the center of a reference point on a patient and the center of the X-ray film holder.

Another object of the invention is to provide an X-ray beam aligning apparatus of simple structure and not requiring complex electronic circuitry.

Another object of the invention is to provide an optical marker for a patient not using a two way mirror in the X-ray beam path with the attendant increased strength of the X-ray beam.

Still another object of the invention is to provide an X-ray beam aligning apparatus and method employing intersecting visible fan beams directed to the surface of the patient facing the X-ray beam.

Yet another object of the invention is to provide an X-ray aligning apparatus employing intersecting fan beam markers which are directed to the patient only and do not traverse other portions of the X-ray room.

Additional objects, advantages, and novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects and in accordance with the purposes of the present invention as described herein, an improved apparatus is provided for positioning an X-ray beam on a patient. The invention includes the novel approach of attaching two fan beam assemblies to the X-ray collimator and directing the fan beams onto the patient to form a cross-hair reticle having a point of intersection coinciding with the center of the X-ray beam and in alignment with the center of the X-ray film holder.

The two fan beams form fan beam planes which bisect the X-ray beam that emerges from the X-ray collimator. The two fan beam planes also mutually perpendicularly bisect one another and form a line of intersection which coincides with the central axis of the X-ray beam. The line of intersection also intersects the point of intersection of the cross-hair reticle of the two fan beams on the patient and is in alignment with the center of the X-ray film holder. In this way, the center of the X-ray beam emerging from the collimator is in alignment with both the reference point on the patient and the center of the film holder.

In accordance with one aspect of the invention, a single indicating visible beam source is attached to the collimator. A beam splitter divides the indicating source beam into two indicating beams. Translating mirrors attached to the X-ray collimator receive one of the two indicating beams and translate it to be perpendicular to the other indicating beam. Each indicating fan beam provides a fan beam plane directed toward the patient and the X-ray film holder to form the cross-hair reticle.

In accordance with another aspect of the invention, two separate fan beam modules are attached to the X-ray collimator. Each module produces an indicating fan beam which provides a fan beam plane. The two fan beam planes bisect the X-ray beam emerging from the collimator and mutually perpendicularly intersect each other to form a line of intersection which coincides with the central axis of the X-ray beam. The line of intersection also intersects the point of intersection of the cross-hair reticle of the two fan beams on the patient and is in alignment with the center of the X-ray film holder. Thus, the center of the X-ray beam emerging from the collimator is in alignment with both the reference point on the patient and the center of the X-ray film holder.

Preferably, the visible light beam source is a laser source. Prior to emergence as a fan beam, the laser light is directed through a spatial filter, a cylindrical lens assembly to provide a fan beam, and a diaphragm to control the width of the fan beam. Control of fan beam width allows the indicating laser to be confined onto the surface of the patient and not to extend past the patient and traverse the X-ray room.

In a further aspect of the present invention, in accordance with its objects and purposes, a method is provided for aligning the central axis of an X-ray beam with the point of intersection of a visible reticle directed to a target. The method comprises the steps of: bisecting the X-ray beam with first and second planar fan beams of visible light parallel to the X-ray beam and directed to the target; and forming a visible reticle on the target by intersecting the first and second fan beams on the target. The point of intersection of the reticle is on the target and is in alignment with the central axis of the X-ray beam.

In another aspect of the present invention, in accordance with its objects and purposes, a method is provided for aligning the central axis of an X-ray beam with the center of an X-ray film holder. The method comprises the steps of: reducing the X-ray beam to a narrow pencil beam coaxial with the central axis of the X-ray beam; placing an X-ray opaque object at the center of the X-ray film holder in front of the X-ray film; directing the point of intersection of the visible reticle onto the center of the X-ray opaque object; directing the pencil X-ray beam toward the opaque object and the film to form a pencil beam spot and an opaque object shadow on the X-ray film; developing the X-ray film and adjusting the aiming of the visible reticle to have the center of the pencil beam spot to coincide with the center of the opaque object shadow; and readjusting the point of intersection of the reticle to coincide with the center of the opaque object shadow. By following these steps, the central axis of the X-ray beam is in alignment with the center of the center of the X-ray film holder when the point of intersection of the cross-hair reticle falls upon the center of the X-ray film holder.

Still other objects of the present invention will become readily apparent to those skilled in this art from the following description wherein there is shown and described a preferred embodiment of this invention, simply by way of illustration of one of the best modes contemplated for carrying out the invention. As it will be realized, the invention is capable of other different embodiments, and its several details are capable of modifications in various obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the descriptions serve to explain the principles of the invention. In the drawings.

DETAILED DESCRIPTION OF THE INVENTION

Figure 1:
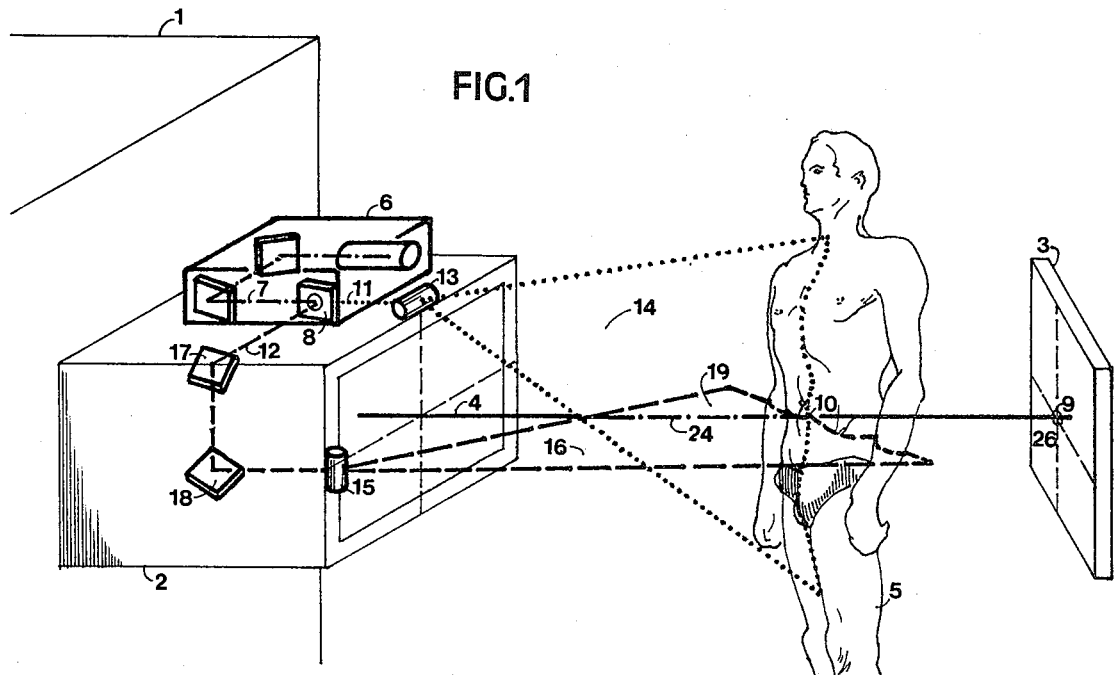
FIG. 1 shows an embodiment of the invention employing one visible beam source.

Reference is now made to FIG. 1 showing an improved X-ray beam positioning apparatus for aligning the X-ray beam of an X-ray machine with both a target and the center of the X-ray film holder. The X-ray machine has an X-ray tube 1, an X-ray collimator 2, and an X-ray film holder 3. A total X-ray beam is represented by the X-ray beam 4 coinciding with the central axis of the total X-ray beam. The X-ray beam emerges from the collimator 2; penetrates target 5, depicted as a human patient; and exposes X-ray film in X-ray film holder 3.

In accordance with the invention, an X-ray beam positioning apparatus is provided which includes a visible light beam source 6 attached to the X-ray collimator 2 and providing a beam of visible light 7. A beam splitter 8 receives the source beam 7 and provides a first indicating beam 11 and a second indicating beam 12. First indicating beam 11 is received at first beam assembly 13 and is converted into a fan beam 14. Second indicating beam 12 is translated by first translating mirror 17 and by second translating mirror 18 and is received by second beam assembly 15. Second fan beam plane 16 emerges from fan beam assembly 15. Fan beam assemblies 13 and 15 are positioned so that first and second fan beam planes 14 and 16 are perpendicular to one another and are directed to both the target 5 and the center 9 of the X-ray film holder 3. Fan beam planes 14 and 16 intersect upon the target 5 forming a cross-hair reticle having a center at point 10.

Figure 2:
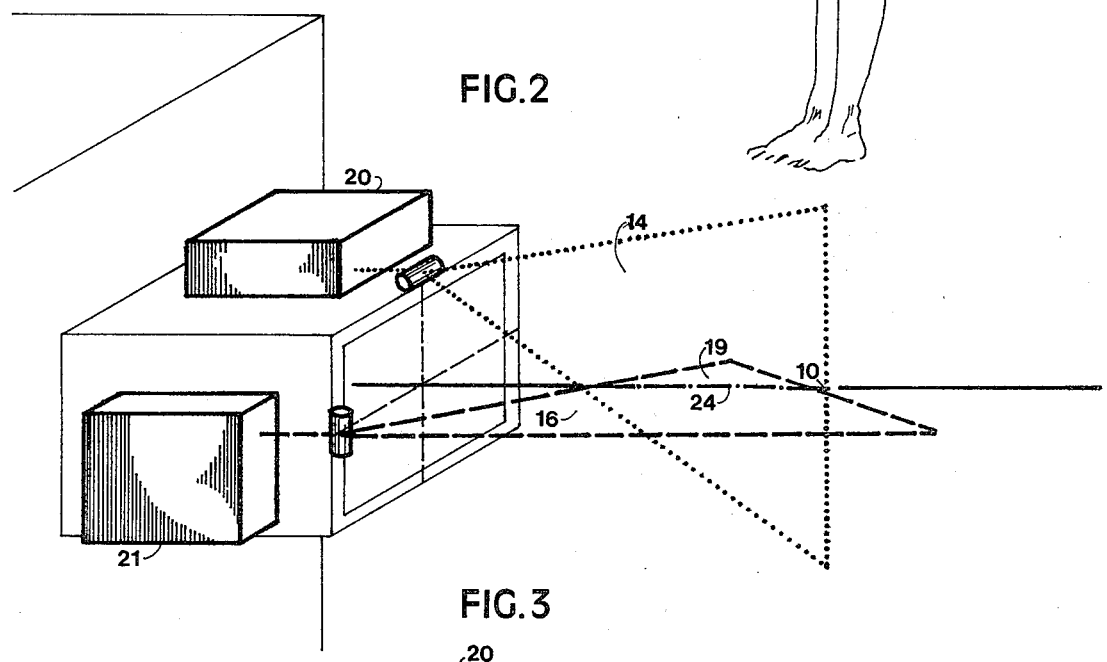
FIG. 2 shows an embodiment of the invention employing two visible beam sources.

In FIG. 2, the first fan beam plane 14 is provided by first beam module 20. Second fan beam plane 16 is provided by second fan beam module 21. The line of intersection 24 is formed by the intersection of fan beams 14 and 16. The line of intersection 24 coincides with the central axis 4 of the X-ray beam.

Preferably, the visible light sources 6, 20, and 21 are laser beams.

Figure 3:
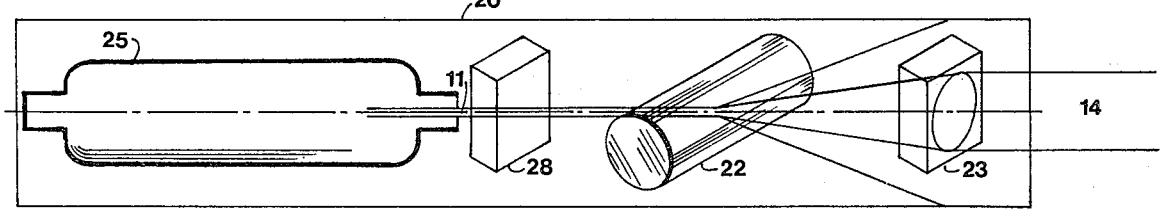
FIG. 3 shows the inner structures of one of the two beam sources.

As shown in FIG. 3, first fan beam module 20 includes a laser source 25 sending a beam 11 through spatial filter 28 and cylindrical rod 22 which converts the straight beam 11 into fan beam 14. Diaphragm 23 limits the width of fan beam 14 so that when it falls on target 5 it does not extend beyond the confines of the surface of the target 5 and does not permeate into the room. Fan beam assemblies 13 and 15 shown in FIG. 1 are comprised of a glass rod 22 and a diaphragm 23 similar to those shown in FIG. 3 for fan beam module 20.

When fan beam assemblies 13 and 15 are installed on X-ray collimator 2, care is taken to assure that the first fan beam plane 14 bisects the X-ray beam in one direction, and the second fan beam plane 16 bisects the X-ray beam perpendicular to the first fan beam plane 14. As a consequence of first beam plane 14 perpendicularly bisecting second beam plane 16, the line of intersection 24 coincides with the central axis of the X-ray beam 4. In this way, a cross-hair reticle 19 is formed on the target 5; and the point 10 of intersection of the cross-hairs of the reticle is in alignment with the central axis 4 of the X-ray beam. In accordance with the invention, both the origin point 10 of the cross-hair reticle and the center 9 of the X-ray film holder 3 are in alignment with the central axis 4 of the X-ray beam.

In a particular apparatus constructed according to the invention, visible source 7 includes a neon-helium gas laser delivering 0.2 MW of radiated power in the 6328 Å red spectrum. Beam splitter 8 is a 30/30/30 transmission mirror which is mounted on a plastic block and which intersects laser beam 7. Suitable fan beam lenses 22 are glass rods 0.5 inches long and 0.125 inches in diameter.

In accordance with another aspect of the invention, a method is provided for aligning the central axis 4 of the X-ray beam with the center 9 of the X-ray film holder 3. The method of aligning comprises the steps: a. reducing the X-ray beam to a narrow pencil beam coaxial with the central axis 4 of the X-ray beam; b. placing an X-ray opaque object 26 at the center 9 of the X-ray film holder 3 in front of the X-ray film; c. directing the point 10 of intersection of a visible reticle 19 onto the X-ray opaque object 26, wherein the point 10 of intersection is in substantial alignment with the central axis 4 of the X-ray beam; d. directing the pencil X-ray beam toward the opaque object 26 and the X-ray film to form a pencil beam spot and an opaque object shadow on the X-ray film; e. developing the X-ray film to observe whether the pencil beam spot is centrally located with respect to the opaque object shadow; f. reaiming the visible reticle 19 to have the center of the pencil beam spot coincide with the center of the opaque object shadow; and g. readjusting the point 10 of intersection of the reticle 19 to coincide with the center of the opaque object shadow. By following the steps of the method, the central axis 4 of the X-ray beam is in alignment with the center 9 of the X-ray film holder 3 when the point 10 of intersection of the visible reticle 19 is directed to the center 9 of the X-ray film holder.

When a target 5, for example a patient, is subjected to X-ray treatment, the point 10 of intersection of the cross-hair reticle 19 on the patient 5 is in alignment with both the center axis 4 of the X-ray beam and the center 9 of the X-ray film holder 3.

In summary, numerous benefits from employing the concepts of the invention have been described. With the invention, the central axis 4 of the X-ray beam is in alignment with both the point 10 of intersection of the cross-hair reticle 19 on the target 5 and the center 9 of the X-ray film holder 3. A method is described whereby the alignment of the X-ray beam 4, target 5, and the X-ray film holder 3 is assured. A single laser source 6 may be employed in conjunction with a beam splitter 8 and translating mirrors 17 and 18 to provide perpendicularly bisecting fan beam planes 14 and 16. Alternatively, two laser modules 20 and 21 may be employed to provide intersecting fan beams 14 and 16. The line of intersection of fan beams 14 and 16 coincides with central axis 4 of the X-ray beam. Glass rods 22 provide fan beams, and diaphragms 23 limit the length the fan beams so that they are confined only to the surface of the target 5 and do not permeate the room.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one with ordinary skill in the art to best utilize the invention in various embodiments and with various modifications as are suitable to the particular use contemplated. It is intended that the scope of the invention be defined by the claims appended hereto.

I claim:

1. For an X-ray machine having an X-ray tube, an X-ray collimator, and an X-ray film holder, an apparatus for positioning an X-ray beam in alignment with a target and the center of the X-ray film holder, comprising:
a visible light beam source attached to the X-ray collimator and providing a source beam;
a beam splitter receiving said source beam and providing a first and second indicating beam;
fan beam assembly means attached to the X-ray collimator and receiving said first and said indicating beams and providing a first fan beam and a second fan beam perpendicular to said first fan beam, wherein said first and second fan beams are directed to both the target and the center of the X-ray film holder and intersect upon the target forming a cross-hair reticle.

2. An X-ray positioning apparatus as described in claim 1 wherein said fan beam assembly means includes:
a first fan beam assembly receiving said first indicating beam and providing a first fan beam directed to the target;
a second fan beam assembly receiving said second indicating beam and providing a second fan beam directed to the target; and
translating mirror means attached to the X-ray collimator and receiving said second indicating beam and translating said second indicating beam to be perpendicular to said first indicating beam.

3. An X-ray positioning apparatus as described in claim 2 wherein:
said first fan beam forms a first beam plane that bisects the X-ray beam that emerges from the X-ray collimator;

said second fan beam forms a second beam plane that bisects the X-ray beam; and said first and second fan beam planes mutually perpendicularly bisect each other and form a line of intersection which coincides with the central axis of the X-ray beam.

4. An X-ray positioning apparatus as described in claim 1 wherein said visible light beam source is a laser source and said fan beam assembly means include a spatial filter, a cylindrical lens assembly producing a fan beam, and a diaphragm controlling the width of said fan beam.

5. A method of aligning the central axis of an X-ray beam with the center of an X-ray film holder, comprising the steps of:

reducing the X-ray beam to a narrow pencil beam coaxial with the central axis of the X-ray beam;

placing an X-ray opaque object at the center of the X-ray film holder in front of the X-ray film;

directing the point of intersection of a visible reticle onto the X-ray opaque object, wherein the point of intersection is in substantial alignment with the central axis of the X-ray beam;

directing the pencil X-ray beam toward the opaque object and the X-ray film to form a pencil beam spot and an opaque object shadow on the X-ray film;

developing the X-ray film to observe whether the pencil beam spot is centrally located with respect to the opaque object;

reaiming the visible reticle to have the center of the pencil beam spot to coincide with the center of the opaque object shadow; and readjusting the point of intersection of the reticle to coincide with the center of the opaque object shadow, thereby providing that the central axis of the X-ray beam is in alignment with the center of the X-ray film holder when the point of intersection of the visible reticle is directed to the center of the X-ray film holder.

* * * * *